United States Patent
Qu et al.

(10) Patent No.: US 7,429,391 B2
(45) Date of Patent: Sep. 30, 2008

(54) HOLISTIC COMPOSITION AND METHOD FOR REDUCING SKIN PIGMENTATION

(75) Inventors: Di Qu, Ada, MI (US); John V. Scimeca, Kentwood, MI (US); Louise M. Schneider, Rockford, MI (US); Jay R. Dittmer, Ada, MI (US); Ronald J. Sharpe, Grand Rapids, MI (US)

(73) Assignee: Access Business Group International LLC, Ada, MI (US)

( * ) Notice: Subject to any disclaimer, the term of this patent is extended or adjusted under 35 U.S.C. 154(b) by 267 days.

(21) Appl. No.: 10/769,556

(22) Filed: Jan. 30, 2004

(65) Prior Publication Data

US 2005/0169860 A1 Aug. 4, 2005

(51) Int. Cl.
- A61K 8/18 (2006.01)
- A61K 6/00 (2006.01)
- A61K 19/02 (2006.01)
- A61K 5/08 (2006.01)

(52) U.S. Cl. .......................................... 424/401; 424/63
(58) Field of Classification Search .................. 424/62, 424/63, 401
See application file for complete search history.

(56) References Cited

U.S. PATENT DOCUMENTS

| | | | |
|---|---|---|---|
| 4,278,656 A | 7/1981 | Nagai et al. | |
| 4,369,174 A | 1/1983 | Nagai et al. | |
| 4,919,921 A | 4/1990 | Hatae | |
| 4,990,330 A | 2/1991 | Oyama | |
| 5,427,775 A | 6/1995 | Sakai et al. | |
| 5,514,367 A | 5/1996 | Lentini et al. | |
| 5,560,907 A | 10/1996 | Sakai et al. | |
| 5,607,692 A | 3/1997 | Ribier et al. | |
| 5,609,875 A | 3/1997 | Hadas | |
| 5,637,293 A | 6/1997 | Honda | |
| 5,773,014 A | 6/1998 | Perrier et al. | |
| 5,824,327 A | 10/1998 | Whittemore et al. | |
| 5,869,031 A | 2/1999 | Tarroux et al. | |
| 5,879,665 A | 3/1999 | Fuller | |
| 5,919,436 A | 7/1999 | Fuller | |
| 5,932,612 A | 8/1999 | Gordon et al. | |
| 5,958,437 A * | 9/1999 | Zaveri ........................ 424/401 |
| 5,980,904 A | 11/1999 | Leverett et al. | |
| 5,989,576 A | 11/1999 | Fuller | |
| 6,057,360 A | 5/2000 | Gordon et al. | |
| 6,077,503 A | 6/2000 | Dornoff | |
| 6,096,295 A | 8/2000 | Fuller | |

(Continued)

FOREIGN PATENT DOCUMENTS

EP 0703776 1/1995

(Continued)

OTHER PUBLICATIONS

Skin Bleaching Ingredients, "Skin Whitening Ingredients", obtained at the internet address: <http://www.medidermlab.com/whiteagent.htm>, Sep. 29, 2003, 6 pages.

*Primary Examiner*—Carlos A. Azpuru
(74) *Attorney, Agent, or Firm*—Brinks Hofer Gilson & Lione

(57) ABSTRACT

The present invention provides a holistic composition and method for reducing skin pigmentation.

18 Claims, 5 Drawing Sheets
(2 of 5 Drawing Sheet(s) Filed in Color)

U.S. PATENT DOCUMENTS

| | | | |
|---|---|---|---|
| 6,110,448 A | 8/2000 | Fuller | |
| 6,123,959 A | 9/2000 | Jones et al. | |
| 6,130,200 A * | 10/2000 | Brodbeck et al. | 514/2 |
| 6,190,664 B1 | 2/2001 | Damperiou | |
| 6,214,352 B1 | 4/2001 | Matsukawa | |
| 6,280,754 B1 | 8/2001 | Hanada et al. | |
| 6,338,855 B1 | 1/2002 | Albacarys et al. | |
| 6,348,204 B1 | 2/2002 | Touzan | |
| 6,436,378 B1 | 8/2002 | Mahashabde et al. | |
| 6,495,122 B2 | 12/2002 | Fankhauser et al. | |
| 6,521,267 B1 | 2/2003 | Steck | |
| 6,641,845 B1 | 11/2003 | Kyrou et al. | |
| 6,699,464 B1 | 3/2004 | Popp et al. | |
| 2001/0046506 A1 | 11/2001 | Rhoades | |
| 2002/0028844 A1 * | 3/2002 | Fitzpatrick et al. | 514/474 |
| 2002/0035046 A1 | 3/2002 | Lukenbach et al. | |
| 2002/0106384 A1 | 8/2002 | Zhang et al. | |
| 2002/0141953 A1 | 10/2002 | Ptchelintsev et al. | |
| 2002/0141956 A1 | 10/2002 | Perricone | |
| 2003/0026856 A1 | 2/2003 | Aust et al. | |
| 2003/0053968 A1 | 3/2003 | Wortzman et al. | |
| 2003/0077236 A1 | 4/2003 | Mammone et al. | |
| 2004/0241116 A1 | 12/2004 | Hale | |

FOREIGN PATENT DOCUMENTS

| | | | |
|---|---|---|---|
| EP | 1002515 | | 5/2000 |
| ES | XP002330463 | | 3/2001 |
| FR | 2735688 | | 12/1996 |
| GB | 2259014 | | 3/1993 |
| JP | 59-076007 | | 4/1984 |
| JP | 63303910 | | 4/1989 |
| JP | 07097311 | | 8/1995 |
| JP | 09227353 | | 1/1998 |
| JP | 10007524 | | 1/1998 |
| JP | 10-147515 | | 6/1998 |
| JP | 10-158148 | | 6/1998 |
| JP | 2000256131 | * | 9/2000 |
| JP | 2000-302641 | | 10/2000 |
| JP | 2000290160 | | 10/2000 |
| JP | 2001-106618 | | 4/2001 |
| JP | 2001-199873 | | 7/2001 |
| JP | 2002-179516 | | 6/2002 |
| WO | WO 9834591 | | 8/1998 |
| WO | WO 9949878 | | 10/1999 |
| WO | WO 0057840 | | 10/2000 |
| WO | WO 2004066973 | | 8/2004 |

* cited by examiner

In-Vitro Efficacy after One Week Incubation

Control

Formula

In-Vitro Efficacy after Two Week Incubation
Black Spots: Melanosome-Laden Keratinocytes on the Surface of the Model Skin Control Formula II

HOLISTIC COMPOSITION AND METHOD FOR REDUCING SKIN PIGMENTATION

The present invention relates to a holistic composition and method for reducing skin pigmentation that includes multiple pigmentation inhibitors, cell protectants, and functional ingredient penetration enhancers.

There is a demand for products that reduce skin pigmentation. The ability to reducing skin pigmentation, however, is complicated due to the numerous pathways involved in pigment production.

Melanocytes are pigment producing cells in the skin. Melanocytes produce melanin, or skin pigment, in two forms, the darker eumelanin, and the lighter phaeomelanin. The amount of each type of melanin determines the color and degree of pigmentation in a person's skin.

Melanocytes produce melanin through a series of complex cellular processes involving the conversion of tyrosine to Dopa, shown in FIG. 1. Tyrosinase is the enzyme responsible for this conversion and is the primary enzyme involved in melanin biosynthesis. Dopa is then converted to eumelanin or phaeomelanin by various biochemical pathways. Once melanin is produced, it is transferred from melanocytes, which reside in lower layers of the epidermis, to keratinocytes which are found in the upper layers of the epidermis. This transfer occurs via melanin carrying vesicles called melanosomes.

Tyrosinase production and activity determines the amount of melanin produced. The amount and type of melanin transferred to keratinocytes determines how pigmented a person's skin will appear. Therefore, if one desires to whiten the skin, it is useful to modulate tyrosinase production and activity, melanosome transfer of melanin, as well as the ratio of eumelanin to phaeomelanin.

In addition to providing skin color, melanin serves as a protectant from the sun. Melanin absorbs harmful UV rays so that cell damage resulting from UV induced free radicals is minimized. Therefore, if the amount of melanin is decreased, it is useful to provide an alternate means of UV protection.

Accordingly, there is a need to reduce skin pigmentation by modulating multiple steps in the melanin production and transfer pathways as well as means for protecting the skin once the pigmentation has been reduced. In addition, a means of increasing penetration of functional ingredients is also desirable.

The holistic approach of the present invention improves the efficacy of skin whitening through the combined effect of the functional ingredients forming the composition of the present invention, whose functions address the multiple aspects of skin pigment production and transfer in addition to providing cell protection and enhanced penetration of the functional ingredients.

In one aspect, the presently claimed invention is a composition for reducing pigmentation in skin. The composition includes the functional ingredients; a tyrosinase production inhibitor, a tyrosinase activity inhibitor, a competitive inhibitor of melanin polymerization, a component that inhibits the transfer of melanin to a keratinocyte, a component to alter the ratio of eumelanin to phaeomelanin, and a component to lighten the skin through exfoliation. In addition, the composition may contain a cell protectant that includes the functional ingredients; a matrix metalloproteinase inhibitor, an antioxidant, a sun protectant, a cell metabolism stimulant, and an inflammation inhibitor. The composition may also include at least one functional ingredient penetration enhancer. The functional ingredient penetration enhancer may be a water soluble and/or an oil soluble ingredient.

In a second aspect, the presently claimed invention relates to a method for reducing pigmentation in skin. The method includes applying a composition to the skin. The composition includes the functional ingredients; a tyrosinase production inhibitor, a tyrosinase activity inhibitor, a competitive inhibitor of melanin polymerization, a component that inhibits the transfer of melanin to a keratinocyte, a component to alter the ratio of eumelanin to phaeomelanin, and a component to lighten the skin through exfoliation. In addition, the composition may contain a cell protectant that includes the functional ingredients; a matrix metalloproteinase inhibitor, an antioxidant, a sun protectant, a cell metabolism stimulant, and an inflammation inhibitor. The composition may also include at least one functional ingredient penetration enhancer. The functional ingredient penetration enhancer may be a water soluble and/or an oil soluble ingredient.

BRIEF DESCRIPTION OF THE DRAWINGS

The patent or application file contains at least one drawing executed in color. Copies of this patent or patent application publication with color drawings(s) will be provided by the Office upon request and payment of the necessary fee.

DETAILED DESCRIPTION

Figure 1:
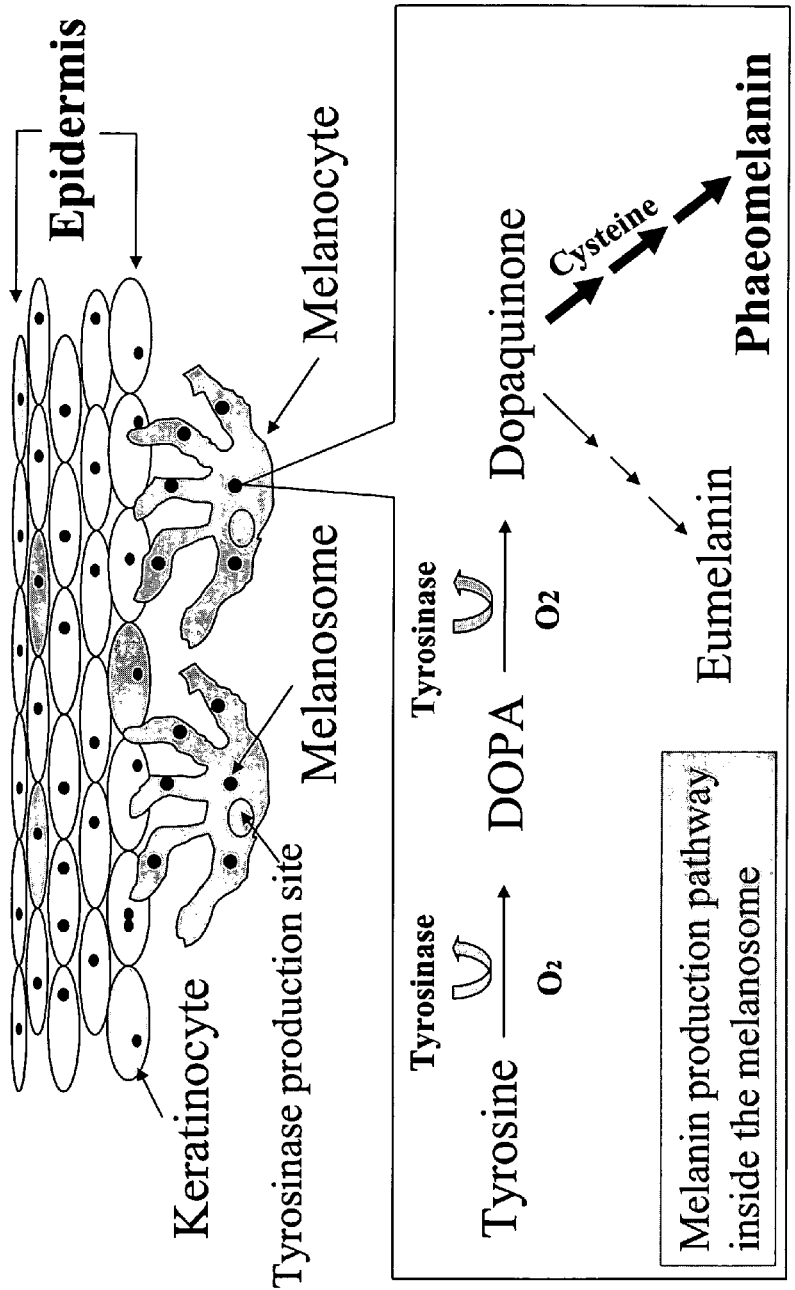
FIG. 1 is an illustration of the melanin production pathway.

The present invention provides a holistic composition and a method for reducing skin pigmentation. This holistic approach involves inhibiting melanin production and transfer at numerous points along the biosynthetic pathway. As decreasing pigmentation in the skin leaves the skin vulnerable to UV and oxidative effects, the holistic approach also provides skin protectants. In addition, enhancing the penetration of these functional ingredients is also contemplated by this holistic approach.

Therefore, the invention comprises 3 broad aspects: (I) pigmentation mechanism inhibitors; (II) cell protectants; and (III) functional ingredient penetration enhancers.

The pigmentation mechanism inhibitors of the present invention include: (1) inhibition of tyrosinase production, (2) tyrosinase activity inhibitors, (3) melanin polymerization inhibitors, (4) modifiers of the ratio of eumelanin to phaeomelanin, (5) transfer of melanosomes from melanocytes to keratinocytes inhibitors, and (6) skin exfoliators.

Inhibition of tyrosinase production is one way to reduce skin pigmentation as decreasing production of the enzyme will result in decreased melanin production. Tyrosinase production inhibitors include, but are not limited to hexapeptide-2.

Inhibition of tyrosinase activity is likewise, a useful means of reducing melanin production. The following compounds, either alone or in combination, may be useful tyrosinase activity inhibitors suitable for the present invention: ascorbic acid and its derivatives, such as alkyl esters of L-ascorbic acid such as L-ascorbyl palmitrate, L-ascorbyl isopalmitate, L-ascorbyl dipalmitate, L-ascorbyl isostearate, L-ascorbyl distearate, L-ascorbyl diisostearate, L-ascorbyl myristate, L-ascorbyl isomyristate, L-ascorbyl 2-ethylhexanoate, L-ascorbyl di-2-ethylhexanoate, L-ascorbyl oleate and L-ascorbyl dioleate; phosphates of L-ascorbic acid such as L-ascorbyl-2-phosphate and L-ascorbyl-3-phosphate; sulfates of L-ascorbic acid such as L-ascorbyl-2-sulfate and L-acorbyl-3-sulfate; their salts with alkaline earth metals such as calcium, sodium and magnesium; kojic acid; *arctostaphylos uva ursi* (bearberry) leaf extract; *glycyrrhiza glabra* (licorice) extract; *sanguisorba officinalis* (burnet) extract; *scutellaria baicalensis* root (skull cap) extract; and *morus alba* (mulberry) extract.

Competitive inhibition of melanin polymerization is another method of reducing melanin production. Compounds, such as those rich in cafeic acid, which compete with DOPA in the polymerization process slow down the rate of DOPA polymerization and therefore lead to decreased melanin production. The following ingredients, either alone or in combination, may be used to competitively inhibit melanin polymerization: extracts rich in cafeic acid; and *helianthus annus* (sunflower) seed extract.

Another way to reduce the appearance of skin pigmentation is to alter the ratio of eumelanin to phaeomelanin such that the lighter phaeomelanin predominates. One example of an ingredient capable of altering the eumelanin to phaeomelanin ratio is *triticum vulgare* (wheat) germ extract.

Inhibiting melanosomes from transferring melanin from the melanocytes to keratinocytes is another means of reducing the appearance of skin pigmentation. Skin pigmentation is controlled by the amount of melanosomes transferred to the keratinocytes, therefore by inhibiting this transfer, skin pigmentation will appear to be decreased. Botanical extracts containing lectin, including *triticum vulgare* (wheat) germ extracts are useful for inhibiting melanin transfer to keratinocytes.

Lightening the skin through exfoliation is an additional way to reduce the appearance of skin pigmentation. The following ingredients, either alone or in combination, may be used to accelerate skin exfoliation: magnesium ascorbyl phosphate, sodium ascorbyl phosphate, calcium ascorbyl phosphate, *avena sativa* (oat) kernel extract; and glycoproteins.

The cell protectants of the present invention include: (1) matrix metalloproteinase (MMP) inhibitors, (2) anti-oxidants, (3) sun protectants; (4) cell metabolism stimulators; and (5) inflammation and/or post-inflammatory hyperpigmentation inhibitors.

MMP inhibitors are useful as cell protectants. UV rays activate MMPs in the skin. Overactive MMPs degrade collagen and elastin and therefore accelerate the process of skin aging. When MMP activity is inhibited, the skin is protected. *Solanum tuberosum* (potato) extract is one example of an ingredient that is useful for inhibiting MMP activity.

Anti-oxidants are powerful cell protectants. Harmful free radicals are generated by UV rays as well as by normal metabolic processes. Anti-oxidants help to neutralize free radicals and thus protect cell integrity and function. The following ingredients, either alone or in combination, may be used as anti-oxidants: ascorbic acid and derivatives such as sodium and/or magnesium ascorbyl phosphate; *helianthus annus* (sunflower) seed extract; citrus unshiu peel extract; *citrus medica limonum* (lemon) extract; *cucumis sativus* (cucumber) fruit extract; *glycyrrhiza glabra* (licorice) extract; tocopherol, and derivatives of tocopherol such as, Sodium Vitamin E Phosphate (VEP), Lauryl Imino Dipropionic Acid Tocopheryl Phosphate, Tocopheryl Glucoside, Tocopheryl Succinate, Tocophersolan (Tocopheryl Polyethylene Glycol 1000 Succinate), Disodium Lauriminodipropionate Tocopheryl Phosphates, Tocophereth-5,10,12,18, and 50 (polyethylene glycol (PEG) tocopheryl ethers), Sodium Vitamin E Phosphate (VEP), Lauryl Imino Dipropionic Acid Tocopheryl Phosphate, and Disodium Lauriminodipropionate Tocopheryl Phosphates.

Sun protectants, both organic and inorganic, minimize the exposure of the skin to harmful sunlight/UV rays. The following ingredients, either alone or in combination, may be used as UV protectants: octinoxate and titanium dioxide.

Stimulants of cellular metabolism lead to healthier skin that is more resistant to environmental insults. Glycoproteins, for example, are useful ingredients for stimulating cell metabolism.

Inhibitors of inflammation and/or post-inflammatory hyperpigmentation are also useful as cell protectants. The following ingredients, either alone or in combination, may be used to inhibit inflammation and associated hyperpigmentation: alpha glucan oligosaccharide; dipotassium glycyrrhizinate; *glycyrrhiza glabra* (licorice) extract; allantoin; *avena sativa* (oat) kernel extract; *morus alba* (mulberry) extract; and *cucumis sativus* (cucumber) fruit extract.

The holistic approach to reducing skin pigmentation of the present invention also addresses the aspect of delivery of the above functional ingredients. In order to realize the benefits of the functional ingredients, they must be able to penetrate the skin and reach their site of action. Improved penetration of functional ingredients results in a more pronounced reduction in skin pigmentation. The dual penetration enhancing system includes a water soluble penetration enhancer in the water phase of the product and an oil soluble penetration enhancer in the oil phase of the product. An example of a suitable water soluble penetration enhancer is ethoxydiglycol. An example of a suitable oil soluble penetration enhancer is a PPG-12/SMDI copolymer.

The present invention is suitable for reducing overall pigmentation as well as for ameliorating uneven pigmentation. The form that the present invention may take includes, but is not limited to: a cream, a lotion, a toner, a bar, a paste, or any other medium suitable for topical administration to the skin.

The composition of the present invention may be applied to the entire body, including the face. The composition may be applied as needed or alternatively, as part of a skin care routine. Preferably, the composition is applied weekly. More preferably, the composition is applied once or twice daily. When a composition is applied twice daily, the preferred mode is once in the morning and once in the evening. When a composition is applied twice daily, the compositions may be the same or different for each application. For example, the same composition may be applied twice daily or alternately, one composition may be applied in the morning and a second, different composition, may be applied in the evening.

The method of the present invention includes applying the composition described above to the skin.

The following examples are intended to illustrate and not limit the present invention.

EXAMPLE 1

Figure 2:
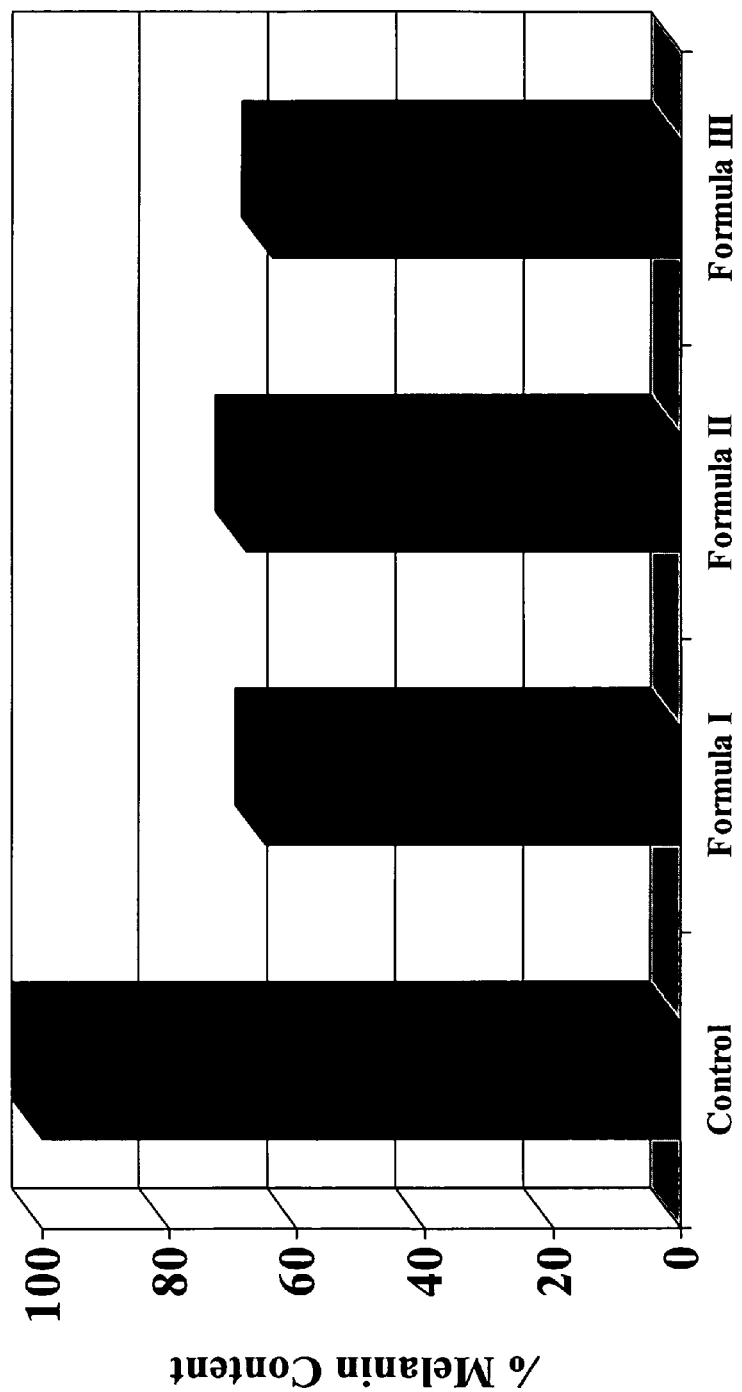
FIG. 2 shows the decreased melanin content in skin samples after treatment with the holistic composition of the presently claimed invention.

An in vitro efficacy test was conducted on a 3-D reconstructed skin model. The skin model contained layers of stratum corneum, epidermis, and dermis. Melanocytes were present in the skin model. Following treatment 3.5 times per week for 3 weeks with one of 3 different formulas of the holistic composition, or a control, the skin samples were analyzed. The melanin content was extracted and measured using a spectrophotometer. The results, shown in FIG. 2, illustrate the reduction in melanin content following treatment with three different formulas of holistic compositions, the active ingredients of which are shown in Tables 1–3. The graph in FIG. 2 illustrates the effectiveness of the present invention in reducing melanin content in skin. All three formulas tested reduced melanin content by over 30% compared to control.

Table 4 shows another exemplary formula. The active ingredients of formulas 1–4 are given in percentage of the total volume. However, one skilled in the art may alter the percentages to suit the particular type of composition desired. Further, the vehicles, buffers, fragrance, etc., that may be used with the present invention are well known and easily determined by one skilled in the art.

TABLE 1

| Active Ingredient | Formula 1 |
| --- | --- |
| Alpha-Glucan Oligosaccharide | 0.50 |
| Dipotassium Glycyrrhizinate | 0.50 |
| Glycoproteins | 0.05 |
| Hydrolyzed Potato Protein | 0.01 |
| Oat Extract | 0.01 |
| Citrus Unshiu Peel Extract | 1.00 |
| Hexapeptide-2 | 0.50 |
| Ethoxydiglycol | 0.50 |
| Sodium Ascorbyl Phosphate | 3.00 |
| Morus Bombycis Extract, Licorice Extract, Sanguisorba Officinalis Extract, Scutellaria Baicalensis Root Extract | 1.50 |
| Lemon Extract, Cucumber Extract, | 0.50 |
| Sunflower Seed Extract | 0.01 |
| Arctostaphylos Uva Ursi Leaf Extract, Magnesium Ascorbyl Phosphate | 0.50 |
| Wheat Germ Extract | 0.01 |
| Allantoin | 0.05 |
| Vehicle, Adjuvants, Cosmeceuticals | Q.S. |
| Total | 100.00 |

TABLE 2

| Active Ingredient | Formula 2 |
| --- | --- |
| Dipotassium Glycyrrhizinate | 0.01 |
| Glycoproteins | 0.05 |
| Hydrolyzed Potato Protein | 0.10 |
| Oat Extract | 0.50 |
| PPG-12/SMDI Copolymer | 0.10 |
| Citrus Unshiu Peel Extract | 1.00 |
| Hexapeptide-2 | 0.05 |
| Ethoxydiglycol | 0.25 |
| Morus Bombycis Extract, Licorice Extract, Sanguisorba Officinalis Extract, Scutellaria Baicalensis Root Extract, | 0.50 |
| Sodium Ascorbyl Phosphate | 3.00 |
| Lemon Extract, Cucumber Extract | 0.50 |
| Sunflower Seed Extract | 0.05 |
| Tocopheryl Acetate | 1.0 |
| Arctostaphylos Uva Ursi Leaf Extract, Magnesium Ascorbyl Phosphate, Water, Glycerin | 0.10 |
| Wheat Germ Extract | 0.05 |
| Allantoin | 0.10 |
| Vehicle, Adjuvants, Cosmeceuticals | Q.S. |
| Total | 100.00 |

TABLE 3

| Active Ingredient | Formula 3 |
| --- | --- |
| Glycoproteins | 0.05 |
| Hydrolyzed Potato Protein | 0.10 |
| Oat Extract Water | 1.00 |
| Citrus Unshiu Peel Extract | 1.00 |
| Hexapeptide-2 | 0.05 |
| Ethoxydiglycol | 0.25 |
| PPG-12/SMDI Copolymer | 0.25 |
| Morus Bombycis Extract, Licorice Extract, Sanguisorba Officinalis Extract, Scutellaria Baicalensis Root Extract | 0.50 |
| Sodium Ascorbyl Phosphate | 3.00 |
| Lemon Extract, Cucumber Extract | 0.50 |
| Sunflower Seed Extract | 0.05 |
| Tocopheryl Acetate | 0.50 |
| Actostaphylos Uva Ursi Leaf Extract, Magnesium Ascorbyl Phosphate | 0.1 |
| Wheat Germ Extract | 0.05 |
| Vehicle, Adjuvants, Cosmeceuticals | Q.S. |
| Total | 100.00 |

TABLE 4

| Active Ingredient | Formula 4 |
| --- | --- |
| Titanium Dioxide | 7.0 |
| Dipotassium Glycyrrhizinate | 0.02 |
| Glycoproteins | 0.01 |
| Hydrolyzed Potato Protein | 0.01 |
| Oat Extract | 0.01 |
| Octinoxate | 7.50 |
| Citrus Unshiu Peel | 1.00 |

TABLE 4-continued

| Active Ingredient | Formula 4 |
|---|---|
| Extract | |
| Hexapeptide-2 | 0.50 |
| Ethoxydiglycol | 0.50 |
| Sunflower Seed Extract | 0.01 |
| Morus Bombycis Extract, Licorice Extract, Sanguisorba Officinalis Extract, Scutellaria Baicalensis Root Extract, | 1.00 |
| Sodium Ascorbyl Phosphate | 3.00 |
| Lemon Extract, Cucumber Extract | 0.50 |
| Tocopherol | 0.10 |
| Arctostaphylos Uva Ursi Leaf Extract, Magnesium Ascorbyl Phosphate | 0.50 |
| Wheat Germ Extract | 0.01 |
| Vehicle, Adjuvants, Cosmeceuticals | Q.S. |
| Total | 100.00 |

Figure 3:
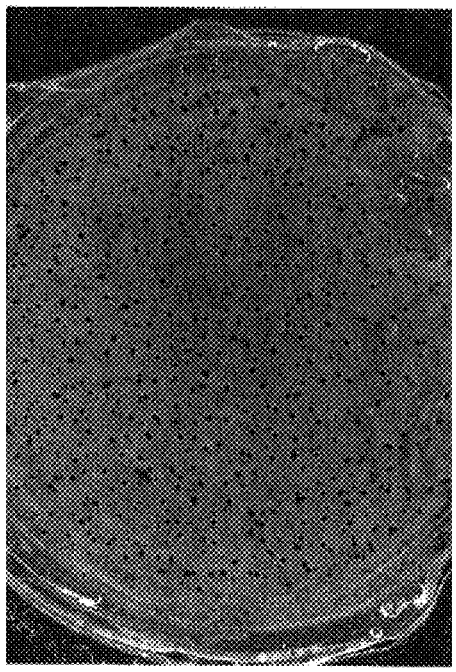
FIG. 3 shows skin models after one week of incubation with a holistic composition of the presently claimed invention.
Figure 3:
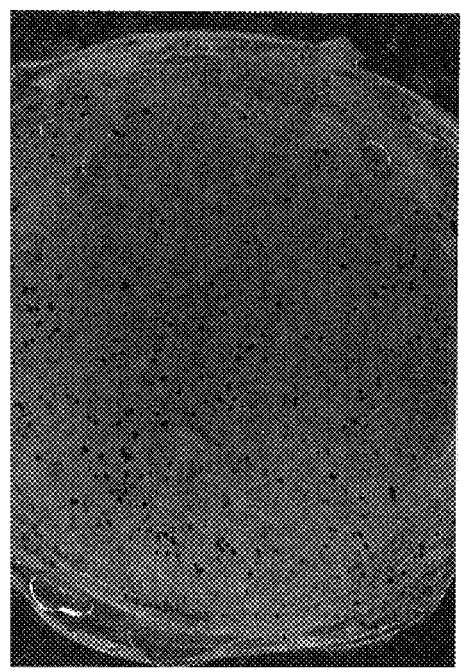
Figure 4:
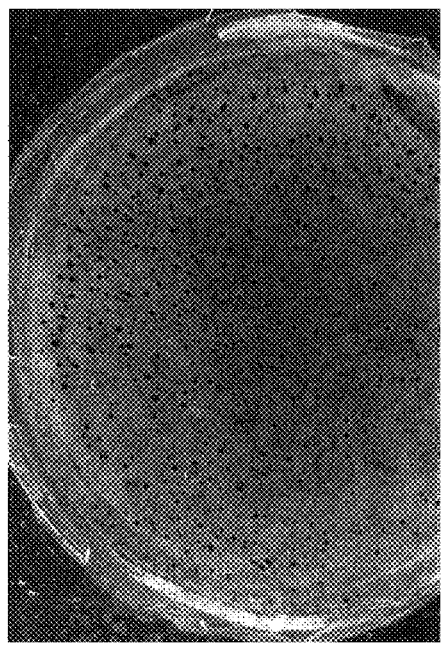
FIG. 4 shows skin models after two weeks of incubation with a holistic composition of the presently claimed invention.
Figure 4:
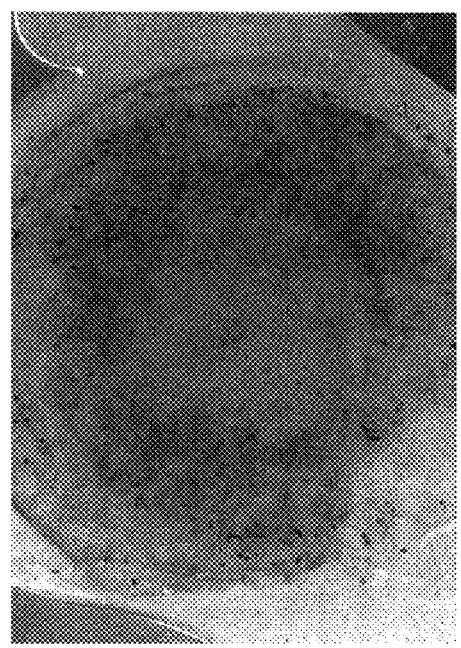

Referring to FIGS. 3 and 4, a 3-D skin model is shown after incubation with a holistic composition of formula 2 for one and two weeks, respectively, compared to control. The black spots in the skin models are melanosome-laden keratinocytes at the surface of the model skin. The model shown is representative of the results obtained in the efficacy testing. The change in the appearance of pigmentation of the treated skin was greater than the percentage change in melanin content. The reason for this is two-fold. Without being bound to any particular theory, it is believed that (1) melanosome transfer inhibition and (2) an alteration of the ratio of eumelanin to phaeomelanin, leading to a predominance of the lighter phaeomelanin, are responsible for the dramatic decrease in the appearance of pigmentation. According to the melanosome transfer inhibition theory, although melanin is still being produced, it is not transferred to the keratinocytes. Therefore, although the melanin is present, it is not visible and the skin appears to be less pigmented than it actually is. Likewise, an alteration in the ratio of eumelanin to phaeomelanin causes the skin to appear lighter. Although the overall melanin content may be the same, skin with phaeomelanin as the predominant form of melanin appears lighter than skin with a higher content of the darker, eumelanin. Therefore, increasing the amount of phaeomelanin and decreasing the amount of eumelanin will cause skin to appear less pigmented. By utilizing a multiple inhibition approach, a dramatic decrease in the appearance of skin pigmentation is achieved.

EXAMPLE 2

Figure 5:
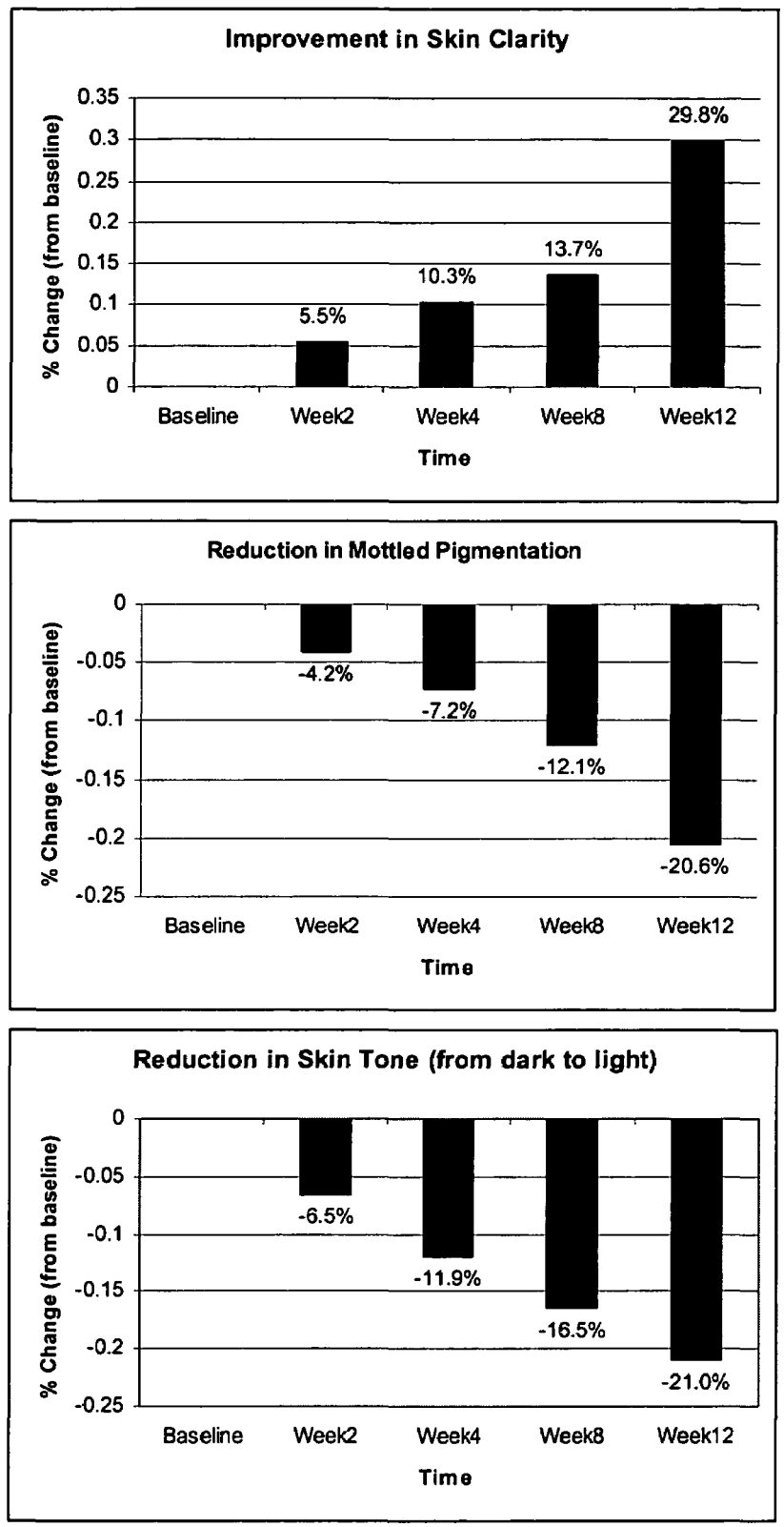
FIG. 5 is a table of results from an in vivo study demonstrating improvements in mottled pigmentation, skin tone and skin clarity.

An in vivo study was conducted in which changes in skin clarity, skin tone and mottled pigmentation were measured. Fifty-six female subjects, were studied for a period of twelve weeks. The subjects were between 25 and 65 years of age and were examined for the presence of mild to moderate mottled hyper-pigmentation on the face. A 10 cm analog scale was used where a score of zero indicated no mottled hyper-pigmentation and a score of ten indicated very dark, extensive pigmentation. Subjects with a score between 3 and 8 qualified to participate in the study and these initial scores were used as baseline values for the study. The subjects were treated with a skin whitening regimen containing four whitening products which were applied twice daily, three products in the morning and three in the evening, for 12 weeks. Changes in mottled pigmentation, skin clarity and skin tone were measured by a clinical grader at 2, 4, 8 and 12 weeks. The results of the study were reported as a percentage change from baseline and are shown in FIG. 5. A significant improvement in skin tone, skin clarity and mottled pigmentation was recorded as early as 2 weeks into the study. By 12 weeks, there was a greater than 20% improvement in skin tone and mottled pigmentation and an almost 30% improvement in skin clarity.

Advantageously, the present invention provides a holistic approach to reducing skin pigmentation by targeting multiple pathways of melanin production and transfer. In addition, cell protectants and enhanced penetration of functional ingredients are also provided.

It is therefore intended that the foregoing detailed description be regarded as illustrative rather than limiting, and that it be understood that it is the following claims, including all equivalents, that are intended to define the spirit and scope of this invention.

We claim:

1. A composition for reducing pigmentation in skin comprising:
   a. a multiple pigmentation inhibitor comprising at least 5 ingredients selected from the group consisting of hexapeptide-2; a tyrosinase activity inhibitor selected from the group consisting of ascorbic acid, derivatives of ascorbic acid, salts of ascorbic acid or its derivatives, kojic acid, *arctostaphylos uva ursi* leaf extract, *glycyrrhiza glabra* extract, *sanguisorba officinalis* extract, *scutellaria baicalensis* root extract, *morus alba* extract, *morus bombycis* extract, and mixtures thereof; a competitive inhibitor of melanin polymerization selected from the group of extracts rich in cafeic acid and *helianthus annus* seed extract; a component that inhibits the transfer of a melanosome to a keratinocyte selected from the group consisting of a botanical extract containing lectin and a *triticum vulgare* germ extract; a component to alter the ratio of eumelanin to phaeomelanin consisting of a *triticum vulgare* germ extract; and a component to lighten the skin through exfoliation selected from the group consisting of sodium ascorbyl phosphate, calcium ascorbyl phosphate, magnesium ascorbyl phosphate, *avena sativa* kernel extract; a glycoprotein, and mixtures thereof;
   b. a cell protectant comprising at least 4 ingredients selected from the group extracts of "*solanum tuberosum* extract", an antioxidant, a sun protectant, a cell metabolism stimulant, and an inflammation inhibitor; and
   c. at least one functional ingredient penetration enhancer selected from the group consisting of a water soluble ingredient and an oil soluble ingredient.

2. The composition of claim 1 wherein the tyrosinase activity inhibitor consists of *arctostaphylos uva ursi* leaf extract.

3. The composition of claim 2 wherein the component that inhibits the transfer of a melanosome to a keratinocyte consists of *triticum vulgare* germ extract.

4. The composition of claim 2 wherein the component to lighten the skin through exfoliation consists of sodium ascorbyl phosphate.

5. The composition of claim 1 wherein the antioxidant is selected from the group consisting of ascorbic acid and derivatives of ascorbic acid, *helianthus annus* seed extract, *citrus unshiu* peel extract, *citrus medica* extract, *cucumis sativus* fruit extract, *glycyrrhiza glabra* extract, tocopherol and derivatives of tocopherol, and mixtures thereof.

6. The composition of claim 1 wherein the sun protectant is selected from the group consisting of octinoxate, titanium dioxide, and mixtures thereof.

7. The composition of claim 1 wherein the cell metabolism stimulant comprises one or more glycoproteins.

8. The composition of claim 1 wherein the inflammation inhibitor includes a post-inflammatory hyperpigmentation inhibitor.

9. The composition of claim 1 wherein the inflammation inhibitor is selected from the group consisting of an alpha glucan oligosaccharide, dipotassium glycyrrhizinate, *glycyrrhiza glabra* extract, allantoin, *avena sativa* kernel extract, *morus alba* extract, *cucumis sativus* fruit extract, and mixtures thereof.

10. The composition of claim 1 wherein the water soluble penetration enhancer comprises ethoxydiglycol.

11. The composition of claim 1 wherein the oil soluble penetration enhancer comprises a PPG-12/SMDI copolymer.

12. The composition of claim 5 wherein the ascorbic acid derivatives are selected from the group consisting of alkyl esters of L-ascorbic acid such as L-ascorbyl palmitate, L-ascorbyl isopalmitate, L-ascorbyl dipalmitate, L-ascorbyl isostearate, L-ascorbyl distearate, L-ascorbyl diisostearate, L-ascorbyl myristate, L-ascorbyl isomyristate, L-ascorbyl 2-ethylhexanoate, L-ascorbyl di-2-ethylhexanoate, L-ascorbyl oleate and L-ascorbyl dioleate; phosphates of L-ascorbic acid such as L-ascorbyl-2-phosphate and L-ascorbyl-3-phosphate; sulfates of L-ascorbic acid such as L-ascorbyl-2-sulfate and L-ascorbyl-3-sulfate; their salts with alkaline earth metals such as calcium, sodium and magnesium, and mixtures thereof.

13. A method for reducing pigmentation in skin comprising applying a composition to the skin, the composition comprising:
 a. a multiple pigmentation inhibitor comprising at least 5 ingredients selected from the group consisting of hexapeptide-2; a tyrosinase activity inhibitor selected from the group consisting of ascorbic acid, derivatives of ascorbic acid, salts of ascorbic acid or its derivatives, kojic acid, *arctostaphylos uva ursi* leaf extract, *glycyrrhiza glabra* extract, *sanguisorba officinalis* extract, *scutellaria baicalensis* root extract, *morus alba* extract, *morus bombycis* extract, and mixtures thereof; a competitive inhibitor of melanin polymerization selected from the group consisting of extracts rich in cafeic acid and *helianthus annus* seed extract; a component that inhibits the transfer of a melanosome to a keratinocyte selected from the group consisting of a *botanical* extract containing lectin and a *triticum vulgare* germ extract; a component to alter the ratio of eumelanin to phaeomelanin consisting of a *triticum vulgare* germ extract; and a component to lighten the skin through exfoliation selected from the group consisting of sodium ascorbyl phosphate, calcium ascorbyl phosphate, magnesium ascorbyl phosphate, *avena sativa* kernel extract, a glycoprotein, and mixtures thereof;
 b. a cell protectant comprising at least 4 ingredients selected from the group consisting of *solanum tuberosum* extract, an antioxidant, a sun protectant, a cell metabolism stimulant, and an inflammation inhibitor; and
 c. at least one functional ingredient penetration enhancer selected from the group consisting of a water soluble ingredient and an oil soluble ingredient.

14. The method of claim 13 wherein the multiple pigmentation inhibitor is comprised of ingredients selected from the group consisting of hexapeptide-2, ascorbic acid, derivatives of ascorbic acid, *arctostaphylos uva ursi* leaf extract, *glycyrrhizinate glabra* extract, *sanguisorba officinalis* extract, *scutellaria baicalensis* root extract, *morus alba* extract, cafeic acid extract, *helianthus annus* seed extract, *triticum vulgare* germ extract, *botanical* extract of lectin and *triticum vulgare* germ, kojic acid, *avena sativa* kernel extract, glycoprotein, and mixtures thereof.

15. The method of claim 13 wherein the cell protectant is comprised of ingredients selected from the group consisting of ascorbic acid and derivatives of ascorbic acid, *helianthus annus* seed extract, *citrus unshiu* peel extract, *citrus medica* extract, *cucumis sativus* fruit extract, *glycyrrhiza glabra* extract, tocopherol and derivatives of tocopherol, *solanum tuberosum* extract, octinoxate, titanium dioxide, one or more glycoproteins, alpha glucan oligosaccharide, dipotassium glycyrrhizinate, allantoin, *avena sativa* kernel extract, *morus alba* extract, and mixtures thereof.

16. The method of claim 14 wherein the functional ingredient penetration enhancer is comprised of ingredients selected from the group consisting of ethoxydiglycol, a PPG-12/SMDI copolymer, and mixtures thereof.

17. The composition of claim 1 wherein the *solanum tuberosum* extract includes hydrolyzed potato protein.

18. The method of claim 13 wherein the *solanum tuberosum* extract includes hydrolyzed potato protein.

* * * * *

UNITED STATES PATENT AND TRADEMARK OFFICE
CERTIFICATE OF CORRECTION

| | | |
|---|---|---|
| PATENT NO. | : 7,429,391 B2 | Page 1 of 1 |
| APPLICATION NO. | : 10/769556 | |
| DATED | : September 30, 2008 | |
| INVENTOR(S) | : Di Qu et al. | |

It is certified that error appears in the above-identified patent and that said Letters Patent is hereby corrected as shown below:

In the Claims

In claim 1, column 8, line 45, immediately after "kernel extract" delete ";" (semicolon) and substitute --,-- (comma) in its place.

In claim 1, column 8, lines 48-49, after "from the group" delete "extracts of 'solanum tuberosum extract', an antioxidant" and substitute --consisting of solanum tuberosum extract, an antioxidant-- in its place.

In claim 12, column 9, line 21, after "L-ascorbyl" delete "palmitrate" and substitute --palmitate-- in its place.

In claim 13, column 10, line 1, after "consisting of" delete "a botanical" and substitute --a botanical-- (no italics) in its place.

Signed and Sealed this

Twenty-third Day of June, 2009

JOHN DOLL
*Acting Director of the United States Patent and Trademark Office*